United States Patent
Fan (10) Patent No.: US 10,520,490 B2
(45) Date of Patent: Dec. 31, 2019

(54) GAS DETECTING DEVICE AND GAS DETECTING METHOD USING THE SAME

(71) Applicant: HTC Corporation, Taoyuan (TW)

(72) Inventor: Fu-Cheng Fan, Taoyuan (TW)

(73) Assignee: HTC Corporation, Taoyuan (TW)

( * ) Notice: Subject to any disclaimer, the term of this patent is extended or adjusted under 35 U.S.C. 154(b) by 42 days.

(21) Appl. No.: 14/820,211

(22) Filed: Aug. 6, 2015

(65) Prior Publication Data

US 2017/0038355 A1    Feb. 9, 2017

(51) Int. Cl.
*G01N 33/497* (2006.01)
*G01N 33/00* (2006.01)

(52) U.S. Cl.
CPC ....... *G01N 33/497* (2013.01); *G01N 33/0073* (2013.01); *G01N 33/4972* (2013.01)

(58) Field of Classification Search
CPC ........... G01N 33/0073; G01N 33/4972; G01N 2033/4975; G01N 2033/4977
See application file for complete search history.

(56) References Cited

U.S. PATENT DOCUMENTS

| | | | |
|---|---|---|---|
| 6,599,253 B1 | 7/2003 | Baum et al. | |
| 6,723,056 B1 | 4/2004 | Alving et al. | |
| 8,313,440 B2 | 11/2012 | Friedman et al. | |
| 2003/0004403 A1* | 1/2003 | Drinan | A61B 5/14539 600/301 |
| 2003/0208133 A1* | 11/2003 | Mault | A61B 5/0002 600/532 |
| 2006/0042965 A1* | 3/2006 | Sasaki | G01N 27/16 205/784 |
| 2008/0056946 A1* | 3/2008 | Ahmad | A61B 5/097 422/68.1 |
| 2010/0043524 A1* | 2/2010 | Takata | B60K 28/063 73/23.3 |
| 2011/0259081 A1* | 10/2011 | Chou | G01N 29/022 73/23.42 |
| 2014/0260541 A1* | 9/2014 | Lakhotia | G01N 27/12 73/25.05 |
| 2014/0276100 A1* | 9/2014 | Satterfield | A61B 5/082 600/476 |

FOREIGN PATENT DOCUMENTS

| | | |
|---|---|---|
| CN | 1094514 A | 11/1994 |
| CN | 1165953 A | 11/1997 |

(Continued)

OTHER PUBLICATIONS

Machine translation of Shockenbaum.*

(Continued)

*Primary Examiner* — Nathaniel J Kolb
(74) *Attorney, Agent, or Firm* — Birch, Stewart, Kolasch & Birch, LLP (57) ABSTRACT

A gas detecting device and a gas detecting method using the same are provided. The gas detecting device includes a casing, a gas detecting element, a first valve, a second valve and a forced exhausting element. The casing has a cavity, an inlet and an outlet. The gas detector is disposed within the cavity. The first valve is for selectively opening or closing the inlet. The second valve is for selectively opening or closing the outlet. The forced exhausting element is disposed within the outlet.

15 Claims, 5 Drawing Sheets

(56) References Cited

FOREIGN PATENT DOCUMENTS

| CN | 1866027 | A | 11/2006 | | |
|----|---------|---|---------|---|---|
| CN | 101819195 | A | 9/2010 | | |
| CN | 102043001 | A | 5/2011 | | |
| CN | 102879439 | A | 1/2013 | | |
| CN | 204044126 | U | 12/2014 | | |
| TW | 201527755 | A | 7/2015 | | |
| WO | WO 2006037283 | A1 * | 4/2006 | ............ | G01N 27/16 |
| WO | WO-2006037283 | A1 * | 4/2006 | ............ | G01N 27/16 |

OTHER PUBLICATIONS

Chen et al., "Chemical Sensors and Electronic Noses Based on 1-D Metal Oxide Nanostructures," IEEE Transactions on Nanotechnology, vol. 7, No. 6, Nov. 2008, pp. 668-682.

* cited by examiner

GAS DETECTING DEVICE AND GAS DETECTING METHOD USING THE SAME

TECHNICAL FIELD

The disclosure relates in general to a gas detecting device and a gas detecting method using the same, and more particularly to a gas detecting device having a forced exhausting element and a gas detecting method using the same.

BACKGROUND

A conventional gas detecting device includes a blowpipe and a flow detector. The user blows a gas to the blowpipe. The flow detector detects the flow of the gas. Since the conventional gas detecting device can only detect the flow, the area of application of the gas detector is restricted.

Therefore, how to expand the area of application of the gas detecting device has become a prominent task for the technology field of the invention.

SUMMARY

The disclosure is directed to a gas detecting device and a gas detecting method using the same which are capable of detecting the ingredients of a to-be-tested gas.

According to one embodiment, a gas detecting device is provided. The gas detecting device includes a casing, a gas detector, a first valve, a second valve and a forced exhausting element. The casing has a cavity, an inlet and an outlet. The gas detector is disposed within the cavity. The first valve is for selectively opening or closing the inlet. The second valve is for selectively opening or closing the outlet. The forced exhausting element is disposed within the outlet.

According to another embodiment, a gas detecting method is provided. The gas detecting method includes following steps. A gas detecting device including a casing, a gas detector, a first valve, a second valve and a forced exhausting element is provided, wherein the casing has a cavity, an inlet and an outlet, the gas detector is disposed within the cavity, the first valve is for selectively opening or closing the inlet, the second valve is for selectively opening or closing the outlet, and the forced exhausting element is disposed within the outlet. A to-be-tested gas is inhaled into the cavity of the gas detecting device by the forced exhausting element. The first valve is controlled to close the inlet. The second valve is controlled to close the outlet. The to-be-tested gas is detected by the gas detector.

The above and other aspects of the invention will become better understood with regard to the following detailed description of the preferred but non-limiting embodiment(s). The following description is made with reference to the accompanying drawings.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

DETAILED DESCRIPTION

Figure 1:
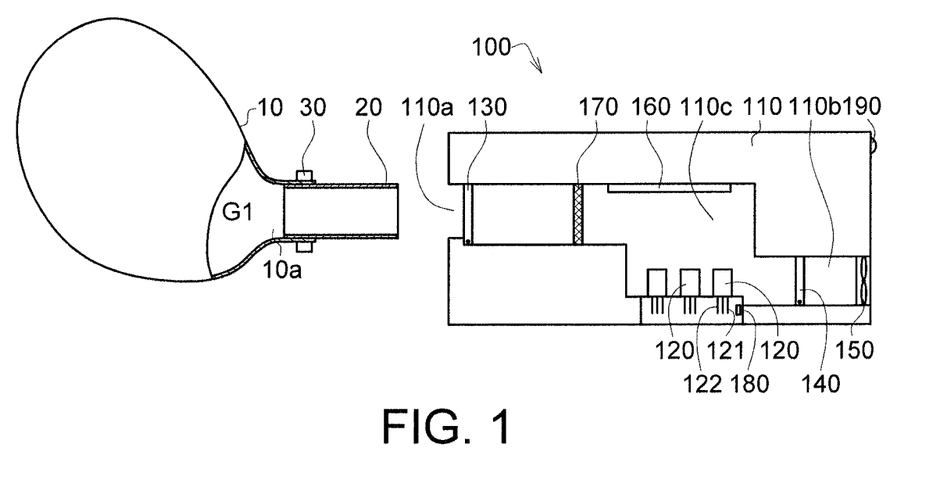
FIG. 1 is a cross-sectional view of a gas detecting device according to an embodiment of the disclosure.

FIG. 1 is a cross-sectional view of a gas detecting device 100 according to an embodiment of the disclosure. The gas detecting device 100 includes a casing 110, at least a gas detector 120, a first valve 130, a second valve 140, a forced exhausting element 150, a heater 160, a filtering element 170, a controller 180 and an indicator 190.

The casing 110 has a cavity 110c, an inlet 110a and an outlet 110b.

The gas detector 120 is disposed within the cavity 110c for detecting the ingredients of a to-be-tested gas G1. In the present embodiment, several gas detectors 120 can be used for detecting specific ingredients of the to-be-tested gas. The controller 180 analyzes these specific ingredients for determining whether the testee has any specific diseases such as chronic obstructive pulmonary disease (COPD), influenza, alcohol concentration, and cancer.

The gas detector 120 includes a number of pins, such as a first pin 121 and a second pin 122. The first pin 121 is a heating pin used for increasing the temperature of the gas detector 120 to form oxygen anions, which generate adsorptive function, decrease the density of the electrons inside the semiconductor and increase the resistance. To put it in greater details, when an adsorptive and reducing gas, such as the natural gas or carbon oxide, replaces adsorptive oxygen with a reducing gas, the electron density of the semiconductor will increase and the resistance will increase accordingly. The above descriptions illustrate the principles of a semiconductor gas detector. Also, the first pin 121 can be heated to a pre-determined temperature (such as 300° C.). The second pin 122 is a signal pin used for outputting a signal S (illustrated in FIG. 3) to the controller 180. The signal S may vary with the temperature. When the signal S reaches a stable value, the stable value can be used as a reference for gas detection.

In addition, the casing 110, possessing thermal insulation or low thermal conductivity, reduces the thermal conduction between the cavity 110c and the outer surface of the casing 110. In another embodiment, the casing 110 can be formed of a material possessing high thermal conductivity. Under such design, the gas detecting device 100 further includes a cladding layer (not illustrated) whose thermal conductivity is lower than that of the casing 110, and also can reduce the thermal conduction between the cavity 110c and the outer surface of the casing 110.

The first valve 130 is disposed within the inlet 110a. The first valve 130 can selectively open or close the inlet 110a according to different timings such as the timing when a gas is inhaled, detected or discharged. Likewise, the second valve 140, disposed within the outlet 110b, can selectively open or close the outlet 110b according to different timings such as the timing when a gas is inhaled, detected or discharged.

The forced exhausting element 150 is disposed within the outlet 110b for inhaling the to-be-tested gas G1 into the cavity 110c or discharging the to-be-tested gas G1 off the casing 110. In an embodiment, the forced exhausting element 150 can be realized by such as a fan. In the present embodiment, although it is exemplified that the forced exhausting element 150 is farther away from the cavity 110c than the second valve 140, the embodiments of the disclosure are not limited to the said exemplification. In another embodiment, the forced exhausting element 150 can be closer into the cavity 110c than the second valve 140.

The heater 160 is disposed within the cavity 110c for increasing the temperature of the cavity 110c so that the time required for heating the first pin 121 of the gas detector 120 to a pre-determined temperature can be shortened. Furthermore, since the heater 160 and the first pin 121 are heated at the same time, the temperature difference between the cavity 110c and the gas detector 120 can be reduced, and the time required for heating the first pin 121 to the pre-determined temperature can be shortened accordingly. In another embodiment, the heater 160 can be omitted.

In the present embodiment, the filtering element 170 is disposed within the inlet 110a. The filtering element 170 can be realized by such as a biological filtration membrane. Before entering the cavity 110c, the to-be-tested gas G1 passes through the filtering element 170 to filter germs, viruses and other particles which may affect the accuracy of gas detection off the to-be-tested gas G1. In the present embodiment, although it is exemplified that the filtering element 170 is closer into the cavity 110c than the first valve 130, the embodiments of the disclosure are not limited to the said exemplification. In another embodiment, the first valve 130 can be closer into the cavity 110c than the filtering element 170.

The controller 180 is for controlling at least one of the heater 160 and the forced exhausting element 150 according to a signal S of the gas detector 120. The controller 180 can also control the on/off state of the first valve 130 and/or the second valve 140.

Figure 2:
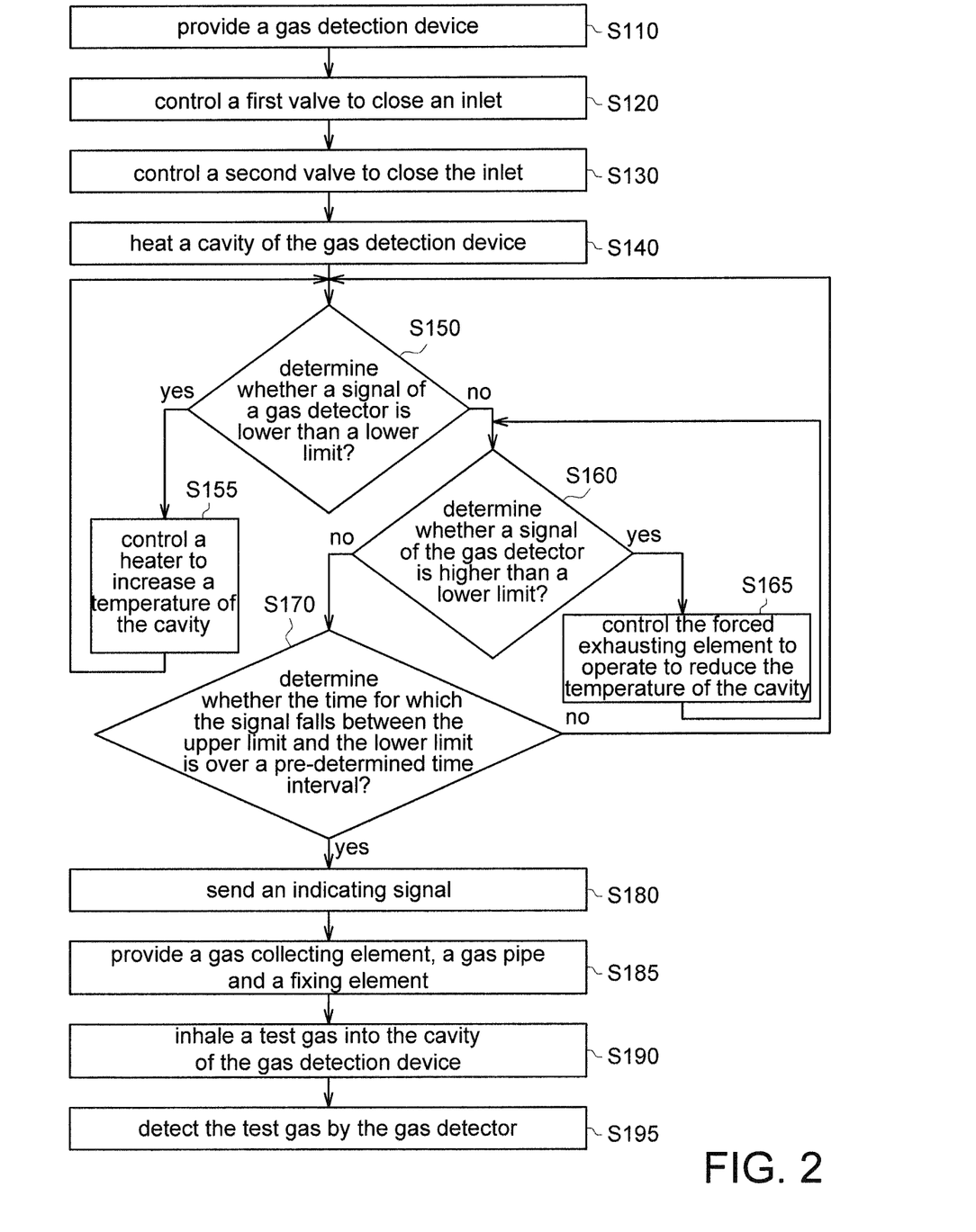
FIG. 2 is a flowchart of a gas detecting method according to an embodiment of the disclosure.

FIG. 2 is a flowchart of a gas detecting method according to an embodiment of the disclosure.

In step S110, the gas detecting device 100 of FIG. 1 is provided.

In step S120, the controller 180 can control the first valve 130 to close the inlet 110a as indicated in FIG. 1.

In step S130, the controller 180 can control the second valve 140 to close the outlet 110b as indicated in FIG. 1.

In step S140, the controller 180 can control the heater 160 to heat the cavity 110c and increase a temperature of the first pin 121 of the gas detector 120. Since the heater 160 heats the cavity 110c and the gas detector 120 at the same time, the temperature difference between the cavity 110c and the gas detector 120 can be reduced, and the time required for heating the gas detector 120 to a pre-determined temperature can be shortened. Thus, the preparation time for gas detection can be reduced.

Figure 3:
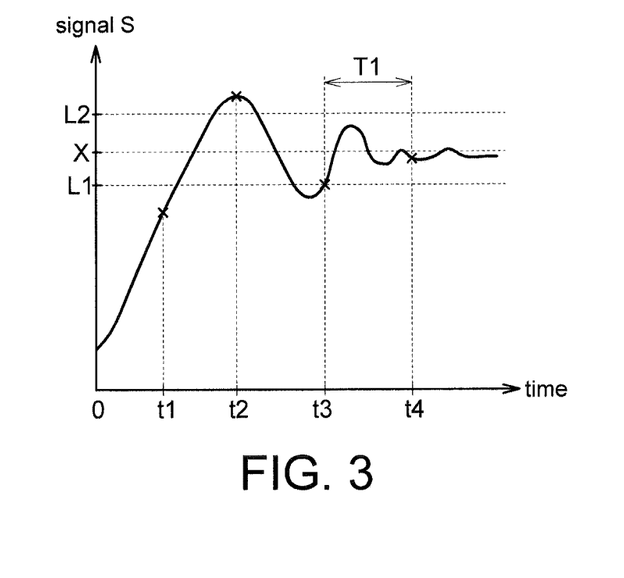
FIG. 3 is a signal output diagram of a second pin of a gas detector of FIG. 1.

In step S150 as indicated in FIG. 3, a signal output diagram of the second pin 122 of the gas detector 100 of FIG. 1 is shown. The controller 180 determines whether an output signal S (such as a voltage signal or a current signal) of the second pin 122 of the gas detector 120 is lower than a lower limit L1. If so, the method proceeds to step S155. If no, the method proceeds to step S160. Suppose the method proceeds to step S155. At time point t1, the signal S is lower than the lower limit L1. This implies that the temperature of the gas detector 120 is too low and the signal S falls within a tolerable range (such as between lower limit L1 and upper limit L2) of a stable value X, and the controller 180 can control the heater 160 to increase a temperature of the cavity 110c (step S155). Then, the method returns to step S150, whether the signal S is lower than the lower limit L1 is determined.

Suppose the method proceeds to step S160. If the output signal S is not lower than the lower limit L1, the controller 180 further determines whether the signal S is higher than the upper limit L2. If so, the method proceeds to step S165. If no, the method proceeds to step S170. Suppose the method proceeds to step S165. At time point t2 (FIG. 3), the signal S is higher than the upper limit L2. This implies that the temperature of the gas detector 120 is too high and the signal S is over the tolerable range of the stable value X. Then, the controller 180 can control the operation of the forced exhausting element 150 to reduce the temperature of the cavity 110c. Then, the method returns to step S160, whether the signal S is higher than the upper limit L2 is determined.

Suppose the method proceeds to step S170. If the signal S is not higher than the upper limit L2, the controller 180 further determines whether the time for which the signal S falls between the upper limit L2 and the lower limit L1 is over a pre-determined time interval T1 (referring to FIG. 3). If so, the method proceeds to step S180. If no, the method returns to step S150. As indicated in FIG. 3, within the pre-determined time interval T1 between time point t3 and time point t4, the signal S stably falls between the upper limit L2 and the lower limit L1. This implies that the signal S stabilizes and the current signal S can be used as a reference for gas detection.

In step S180, when the signal S stabilizes (this implies that the preparation of gas detection is completed, that is, gas detection can be started), the controller 180 controls the indicator 190 to send an indicating signal. In an embodiment, indicating signal can be realized by a color light, a sound or any other signal with indicating function.

In step S185 as indicated in FIG. 1, a gas collecting element 10, a gas pipe 20 and a fixing element 30 are provided. The gas collecting element 10 is for collecting a to-be-tested gas G1. The gas pipe 20 is connected to the opening 10a of the gas collecting element 10. The fixing element 30 can tightly fix the gas pipe 20 and the gas collecting element 10 to avoid the to-be-tested gas G1 being leaked via the connection between the gas pipe 20 and the gas collecting element 10.

In an embodiment, the gas collecting element 10 can be realized by such as an air bag. The gas pipe 20 can be realized by such as a rigid pipe fitting, such that the first valve 130 of the gas detecting device 100 can be pushed to open the inlet 110a for the interior of the gas collecting element 10 to be connected to the inlet 110a. In terms of materials, the gas pipe 20 can be formed of plastics, metal or any other suitable materials, and the fixing element 30 can be realized by such as a buckle, a rubber band or any other suitable fixers.

Figure 4:
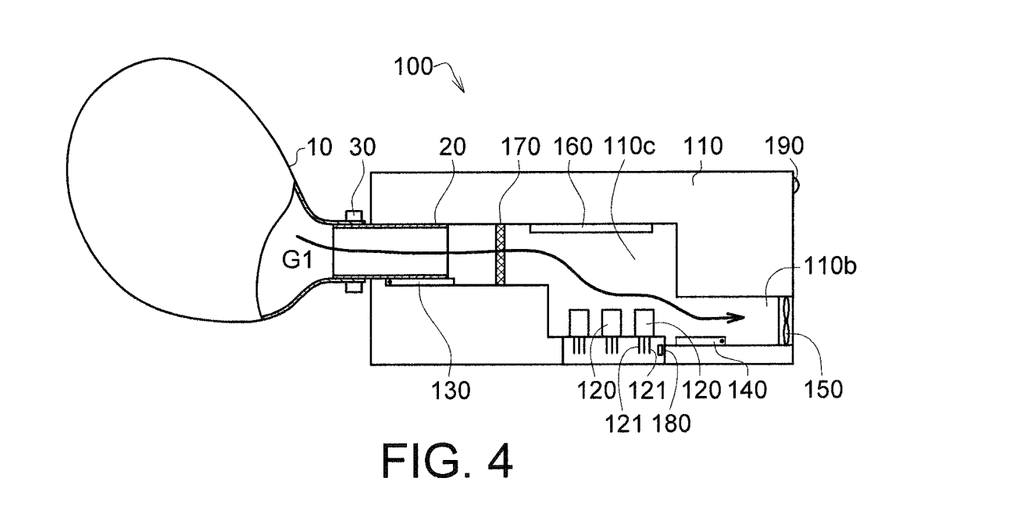
FIG. 4 is a schematic diagram of the gas detecting device of FIG. 1 connected to the gas collecting element.

FIG. 4 is a schematic diagram of the gas detecting device 100 of FIG. 1 connected to the gas collecting element 10. The user can blow a to-be-tested gas G1 to the interior of the gas collecting element 10 through the gas pipe 2. Then, the gas pipe 20 is connected to the gas detecting device 100, such that the interior of the gas collecting element 10 is interconnected with the gas detecting device 100. Since the gas pipe 20 has sufficient hardness or strength, the first valve 130 can be easily pushed to open the inlet 110a.

In step S190, after the gas collecting element 10 is connected to the gas detecting device 100, the controller 180 can control the forced exhausting element 150 to inhale the to-be-tested gas G1 into the cavity 110c from inside the gas collecting element 10. In an embodiment, the control function of the controller 180 can be activated by touching a key. In another embodiment, when the controller 180 detects (by using a suitable sensor for example) that the gas collecting element 10 and the gas detecting device 100 are connected, the controller 180 automatically can control the forced exhausting element 150 to inhale the to-be-tested gas G1 into the cavity 110c from inside the gas collecting element 10.

Before or after inhaling the gas, the controller 180 can control the second valve 140 to open. Or, the controller 180 does not control the second valve 140 to open. Instead, the controller 180 can compulsorily control the attraction of the forced exhausting element 150 to open the second valve 140. During the inhaling process, the to-be-tested gas G1 inside the gas collecting element 10 passes through the filtering element 170 to filter germs, viruses or other particles off the to-be-tested gas G1 to increase the accuracy of gas detection. In another embodiment, the filtering element 170 can be disposed within the gas pipe 20 after the to-be-tested gas G1 is blown to the gas collecting element 10, and similar filtering effect still can be achieved. The embodiments of the disclosure do not restrict the design position of the filtering element 170, and any design position allowing the to-be-tested gas G1 to pass through the filtering element 170 before entering the cavity 110c will do.

During the inhaling process, the controller 180 can continuously control the operation of the heater 160 and/or compulsorily control the forced exhausting element 150 to operate for restricting the signal S (referring to FIG. 3) within the tolerable range of the stable value X.

Figure 5:
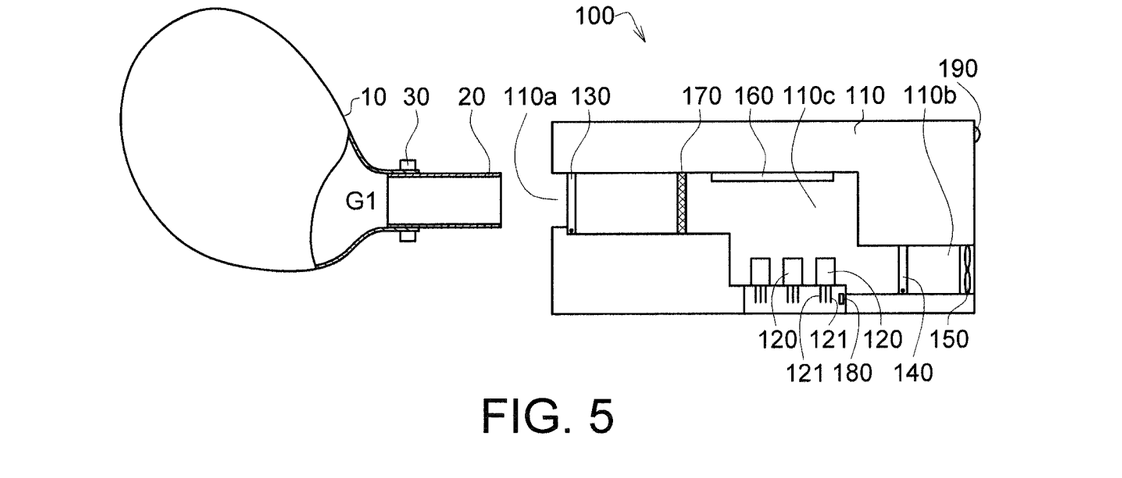
FIG. 5 is a schematic diagram of a gas detector detecting the gas according to an embodiment of the disclosure.

In step S195 as indicated in FIG. 5, a schematic diagram of a gas detector detecting the gas according to an embodiment of the disclosure is shown. After most or a sufficient amount of the to-be-tested gas G1 enters the cavity 110c, the gas detector 120 starts to detect the ingredients of the to-be-tested gas G1. Before the detection process starts, firstly, the gas collecting element 10 and the gas detecting device 100 are separated from each other, and then the controller 180 controls the first valve 130 and the second valve 140 to close to avoid the to-be-tested gas G1 being leaked via the first valve 130 and the second valve 140. In, another embodiment, the first valve 130 has an automatic recovery function (can be implemented by flexible elements), and is automatically closed after the gas collecting element 10 and the gas detecting device 100 are separated. Under such design, the controller 180 does not need to particularly control the first valve 130 to close.

In another embodiment, during the detection process of the to-be-tested gas G1, the gas collecting element 10 can be reserved on the gas detecting device 100 (that is, the connection state between the gas collecting element 10 and the gas detecting device 100 is maintained as illustrated in FIG. 4). Under such design, the first valve 130 is open, and the second valve 140 is closed.

Figure 6:
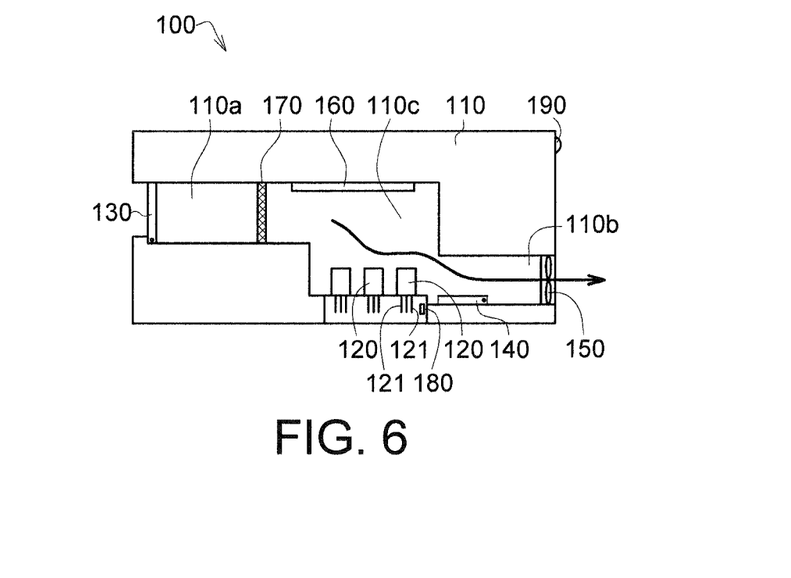
FIG. 6 is a schematic diagram of a forced exhausting element inhaling the gas according to an embodiment of the disclosure.

FIG. 6 is a schematic diagram of a forced exhausting element inhaling the gas according to an embodiment of the disclosure. After gas detection finishes, the controller 180 can control the second valve 140 to open and compulsorily control the forced exhausting element 150 to operate to discharge the to-be-tested gas G1 inside the cavity 110c off the casing 110 lest the to-be-tested gas G1 might be left inside the cavity 110c and negatively affect the accuracy of subsequent gas detection. In another embodiment, the controller 180 can control the first valve 130 and the second valve 140 to open at the same time for discharging the to-be-tested gas G1 off the casing 110 from inside the cavity 110c.

In the above embodiments, it is exemplified that the cavity 110c is heated before the to-be-tested gas G1 is inhaled into the cavity 110c. In another embodiment, it can be exemplified that the to-be-tested gas G1 is inhaled into the cavity 110c before the heater 160 and/or the second pin 112 are controlled to heat the cavity 110c. In terms of the process of FIG. 2, steps S185 and S190 can be performed prior to step S140.

In another embodiment, steps S150, S155, S160, S165 and S170 of FIG. 2 can be omitted. Under such design, whether the preparation of gas detection is completed can be known through the indicating signal of step S180.

Figure 7:
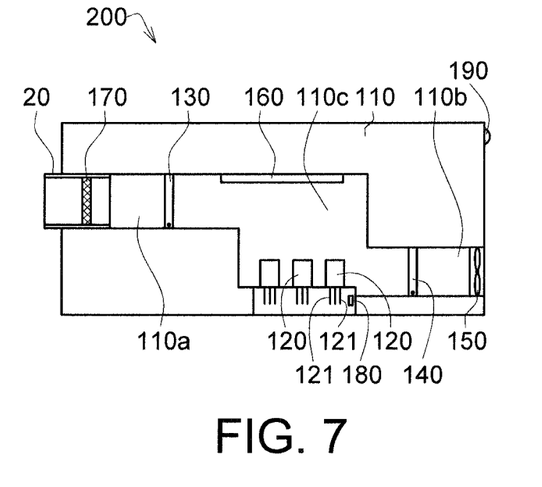
FIG. 7 is a cross-sectional view of a gas detecting device according to another embodiment of the disclosure.

FIG. 7 is a cross-sectional view of a gas detecting device 200 according to another embodiment of the disclosure. The gas detecting device 200 includes a casing 110, at least a gas detector 120, a first valve 130, a second valve 140, a forced exhausting element 150, a heater 160, a filtering element 170, a controller 180, an indicator 190 and a gas pipe 20.

In the present embodiment, the gas pipe 20 can be detachably plugged into or unplugged from the inlet 110a of the casing 110. Thus, during gas detection, the testee only needs to blow a gas to the gas pipe 20 of the gas detecting device 200. Since the gas pipe 20 is disposed on the casing 110, the gas collecting element 10 can be selectively omitted. Besides, the filtering element 170 can be disposed within the gas pipe 20, so that the filtering element 170 and the gas pipe 20 integrally form a disposable element. Thus, after gas detection is completed, the filtering element 170 and the gas pipe 20 can be disposed after use to avoid the to-be-tested gas G1 left on the filtering element 170 negatively affecting the accuracy of subsequent gas detection.

To summarize, the gas detecting device and the gas detecting method using the same disclosed in the embodiments of the disclosure are capable of detecting gas properties such as the ingredients of the gas. In an embodiment, the heater of the gas detecting device can heat the cavity to shorten the time for the preparation of gas detection. In another embodiment, the heater and/or the forced exhausting element of the gas detecting device can operate concurrently or alternatively, such that the signal of the gas detector can quickly reach a stable state and the accuracy of gas detection can be increased. Also, the first valve and/or the second valve of the gas detecting device can be selectively closed or opened to assist the gas detecting device with inhaling, detecting and/or discharging the gas according to according to different timings such as the timing when a gas is inhaled, detected or discharged. In another embodiment, the to-be-tested gas can be collected at the gas collecting element first, and then the gas collecting element is connected to the gas detecting device to perform gas detection after the gas detecting device has completed the preparation of gas detection (for example, when the signal of the gas detector reaches a stable value). In another embodiment, the filtering element and the gas pipe can integrally form a disposable element, which can be disposed after use, to avoid the to-be-tested gas left on the filtering element negatively affecting the accuracy of next gas detection.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A gas detecting device, comprising:
a casing having a cavity, an inlet and an outlet;
a gas detector disposed within the cavity;
a first valve for selectively opening or closing the inlet;
a second valve for selectively opening or closing the outlet;
a forced exhausting element disposed within the outlet; and
a heater disposed within the cavity, wherein the heater faces and is separated from the gas detector,
wherein the inlet, the outlet and the cavity are disposed within the casing, the first valve is disposed within the inlet, the second valve is disposed within the outlet, the casing has an upper surface, a lower surface opposite to the upper surface, a first outer lateral surface and a second outer lateral surface opposite to the first outer lateral surface, the first outer lateral surface and the second outer lateral surface extend between the upper surface the lower surface, and the entire inlet inwardly extends from the lateral surface to the cavity,
wherein the inlet is connected with an upper portion of a lateral side of the cavity, the outlet is connected with a lower portion of an opposite lateral side of the cavity, the outlet and the inlet are staggered with each other up and down, and the gas detector is disposed adjacent to the lower portion, and
wherein the inlet extends straightly to the upper portion of the lateral side of the cavity from the first outer lateral surface, and the outlet extends straightly to the lower portion of the lateral side of the cavity from the second outer lateral surface.

2. The gas detecting device according to claim 1, wherein the filtering element is a biological filtration membrane.

3. The gas detecting device according to claim 1, further comprising:
a gas collecting element for collecting a to-be-tested gas.

4. The gas detecting device according to claim 3, wherein the gas pipe is connected to an opening of the gas collecting element and
the fixing element is for fixing the gas pipe and the gas collecting element.

5. The gas detecting device according to claim 1, further comprising:
a controller configured to:
control at least one of the heater and the forced exhausting element to operate according to a signal from the gas detector.

6. The gas detecting device according to claim 5, wherein the controller is further configured to:
determine whether the signal from the gas detector is higher than an upper limit;
control the forced exhausting element to operate to reduce a temperature of the cavity if the signal from the gas detector is higher than the upper limit;
determine whether the signal from the gas detector is lower than a lower limit; and
control the heater to increase a temperature of the cavity if the signal from the gas detector is lower than the lower limit.

7. The gas detecting device according to claim 6, wherein the controller is further configured to:
determine whether the time for which the signal from the gas detector falls between the upper limit and the lower limit is over a pre-determined time interval; and
send an indicating signal if the time for which the signal of the gas detector falls between the upper limit and the lower limit is over the pre-deteiinined time interval.

8. The gas detecting device according to claim 1, further comprising:
a controller configured to:
control the forced exhausting element to inhale a to-be-tested gas into the cavity.

9. The gas detecting device according to claim 1, further comprising:
a filtering element disposed within the inlet.

10. A gas detecting method, comprising:
providing a gas detecting device, wherein the gas detecting device comprises a casing, a gas detector, a first valve, a second valve, a forced exhausting element and a heater, the casing has a cavity, an inlet and an outlet, the gas detector is disposed within the cavity, the first valve is for selectively opening or closing the inlet, the second valve is for selectively opening or closing the outlet, the forced exhausting element is disposed within the outlet, a heater is disposed within the cavity, and faces and is separated from the gas detector, the inlet, the outlet and the cavity are disposed within the casing, the first valve is disposed within the inlet, the second valve is disposed within the outlet, the casing has an upper surface, a lower surface opposite to the upper surface, a first outer lateral surface and a second outer lateral surface opposite to the first outer lateral surface, the first outer lateral surface and the second outer lateral surface extend between the upper surface the lower surface, the entire inlet inwardly extends from the lateral surface to the cavity, wherein the inlet is connected with an upper portion of a lateral side of the cavity, the outlet is connected with a lower portion of an opposite lateral side of the cavity, the outlet and the inlet are staggered with each other up and down, and the gas detector is disposed adjacent to the lower portion, wherein the inlet extends straightly to the upper portion of the lateral side of the cavity from the first outer lateral surface, and the outlet extends straightly to the lower portion of the lateral side of the cavity from the second outer lateral surface;
inhaling a to-be-tested gas, through the gas pipe, into the cavity of the gas detecting device by the forced exhausting element;
controlling the first valve to close the inlet;
controlling the second valve to close the outlet; and
detecting the to-be-tested gas by the gas detector.

11. The gas detecting method according to claim 10, further comprising:
heating the cavity.

12. The gas detecting method according to claim 10, wherein the gas detecting method further comprises:
controlling the heater and the forced exhausting element to operate according to a signal from the gas detector.

13. The gas detecting method according to claim 12, wherein the step of controlling the heater and the forced exhausting element to operate according to the signal of the gas detector comprises:
determining whether a signal from the gas detector is higher than an upper limit;
controlling the forced exhausting element to reduce a temperature of the cavity if the signal from the gas detector is higher than the upper limit;

determining whether the signal from the gas detector is lower than a lower limit; and controlling the heater to increase a temperature of the cavity if the signal from the gas detector is lower than the lower limit.

14. The gas detecting method according to claim 13, further comprising:

determining whether the time for which the signal from the gas detector falls between the upper limit and the lower limit is over a pre-determined time interval; and sending an indicating signal if the time for which the signal from the gas detector falls between the upper limit and the lower limit is over the pre-determined time interval.

15. The gas detecting method according to claim 10, further comprising:

controlling the forced exhausting element to inhale a to-be-tested gas into the cavity.

* * * * *